United States Patent
Hembre et al.

(12) 
(10) Patent No.: US 6,218,555 B1
(45) Date of Patent: Apr. 17, 2001

(54) PROCESS FOR THE PREPARATION OF ALKANOYLOXY-BENZENESULFONIC ACIDS AND SALTS THEREOF

(75) Inventors: Robert Thomas Hembre, Johnson City; Edwin Franklin Holcombe, III, Morristown; Robert Lin; Mark Robert Shelton, both of Kingsport, all of TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/543,950

(22) Filed: Apr. 6, 2000

Related U.S. Application Data

(60) Provisional application No. 60/152,291, filed on Sep. 3, 1999.

(51) Int. Cl.$^7$ .................................................. C07C 53/00
(52) U.S. Cl. ............................... 554/99; 554/90; 554/177
(58) Field of Search .......................................... 554/90, 99

(56) References Cited

U.S. PATENT DOCUMENTS

| | | |
|---|---|---|
| 2,628,253 | 2/1953 | Dowdall . |
| 3,772,389 | 11/1973 | Lowrance, Jr. . |
| 4,587,054 | 5/1986 | Hardy et al. . |
| 4,588,532 | 5/1986 | Moyne et al. . |
| 4,695,412 | 9/1987 | Balzer et al. . |
| 4,883,612 | 11/1989 | Moyne et al. . |
| 5,069,828 | 12/1991 | Dumas et al. . |
| 5,124,475 | 6/1992 | Nepras et al. . |

OTHER PUBLICATIONS

Allan H. Gilbert, Detergent Age, Jun., 1967, pp 18–20.
Allan H. Gilbert, Detergent Age, Aug., 1967, pp 26–28.
Harold R. W. Ansink et al, Recl. Trav. Chim. Pays–Bas 1992, 111, pp 215–221.
E. J. Bourne et al, Journal of the Chemical Society, 1949, pp 2976–2979.
Bert H. Bakker et al, Eur. J. Org. Chem., 1999, 1, pp 91–96.
Themba E. Tyobeka et al, Tetrahedron, 1988, 44, pp 1971–1978.

*Primary Examiner*—Samuel Barts
*Assistant Examiner*—Diedra Faulkner
(74) *Attorney, Agent, or Firm*—Michael J. Blake; Harry J. Gwinnell

(57) ABSTRACT

Disclosed is a process for the preparation of alkanoate esters of hydroxybenzenesulfonic acids and salts thereof by the steps of (1) contacting or reacting phenol with an alkanoic acid in the presence of trifluoroacetic acid (TFA) and trifluoroacetic anhydride (TFAA) to produce a aryl alkanoate ester and (2) contacting the reaction mixture of step (1) with a sulfonating agent to convert the aryl alkanoate ester to an alkanoate ester of hydroxybenzenesulfonic acid. The process provides the economic advantage inherent in using the product of esterification of step (1) without Disolation in the sulfonation of step (2).

12 Claims, No Drawings

PROCESS FOR THE PREPARATION OF ALKANOYLOXY-BENZENESULFONIC ACIDS AND SALTS THEREOF

CROSS REFERENCE TO RELATED APPLICATION

This application claims the benefit of U.S. Provisional Application No. 60/00152,291, filed Sep. 3, 1999.

FIELD OF THE INVENTION

This invention pertains to a process for the preparation of alkanoate esters of hydroxybenzenesulfonic acids and salts thereof. More specifically, this invention pertains to a process which comprises the steps of (1) contacting or reacting phenol with an alkanoic acid in the presence of trifluoroacetic acid (TFA) and trifluoroacetic anhydride (TFAA) to produce an aryl alkanoate ester and (2) contacting the reaction mixture of step (1) with a sulfonating agent to convert the aryl alkanoate ester to an alkanoate ester of hydroxybenzenesulfonic acid.

BACKGROUND OF THE INVENTION

Alkanoate esters of hydroxybenzenesulfonic acids and salts thereof are useful as bleach activators in detergent compositions (Allan H. Gilbert, *Detergent Age*, 1967, June, pages 18–20 and August, pages 30–33). These ester compounds, also named as alkanoyloxybenzenesulfonic acids and salts thereof, typically are manufactured by contacting a hydroxybenzene-sulfonic acid or salt thereof with a saturated, aliphatic carboxylic (alkanoic) acid, usually an alkanoic acid containing 6 or more carbon atoms, or an ester-forming derivative thereof such as an anhydride or acid halide, under ester forming conditions. Such processes are carried out either in a solvent or the carboxylic acid related to the desired ester product at temperatures of 80 to 200° C. These known methods are well summarized in U.S. Pat. Nos. 4,587,054, 4,588,532, 4,883,612 and 5,069,828. The preferred route for commercial scale synthesis is esterification of sodium 4-phenolsulfonate (SPS) using carboxylic acid anhydrides as the esterification agent. SPS is manufactured by the sulfonation of phenol which initially produces a relatively large (≈40 %) amount of the ortho-hydroxybenzene sulfonic acid. Heating the mixture of ortho- and para-hydroxybenzene sulfonic acids produces a high para (>95%) product, which is neutralized to yield SPS.

An alternative to these methods is the sulfonation of aryl carboxylate esters. An advantage of this alternative is that the sulfonation of a phenyl ester occurs with higher selectivity for the desired para sulfonation product than the sulfonation of phenol described above (see Ansink and Cerfontain *Recl. Trav. Chim. Pays-Bas* 1992, 111, 215). U.S. Pat. Nos. 4,695,412 and 5,124,475 disclose the sulfonation of pre-purified aryl esters with sulfonating agents such as sulfur trioxide, oleum or chlorosulfonic acid to produce the desired alkanoate esters of hydroxybenzene sulfonic acids. The methods described in these patents first require the synthesis and purification of an aryl alkanoate ester. U.S. Pat. No. 3,772,389 describes the prior art in the synthesis and manufacture of aryl esters and discloses a process in which a carboxylic acid and a phenol are combined between the temperatures of 75–285° C. using a borate-sulfuric acid catalyst. E. J. Bourne and coworkers in the *Journal of the Chemical Society* 1949, 2976–79 disclose the use of trifluoroacetic anhydride (TFAA) as an "impeller" in the synthesis of aryl alkanoate esters using milder conditions. It has been discovered that the effectiveness of the TFAA impeller method is increased when trifluoroacetic acid (TFA) is used as a solvent, in particular for the synthesis of hydroxybenzenesulfonate esters, and that the reactions carried out in this fashion occur in very high yield (>95%). In addition, because these TFAA impeller esterificatons occur at ambient temperatures in minutes rather than hours the common problems of color body or other byproduct formation are minimized.

Sulfonation reactions carried out in TFA are not well known but U.S. Pat. No. 2,628,253 discloses that TFA reacts with $SO_3$ to yield the mixed anhydride having the structure

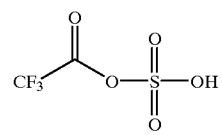

Bert H. Bakker and Hans Cerfontain report in the *Eur. J. Org. Chem.*, 1999, 1, 91–96 that this mixed anhydride reagent can be used for the sulfonation of alkenes. Tyobeka, et al., *Tetrahedron*, 1988, 44, 1971–78, further discloses that the bis-mixed anhydride of TFA and sulfuric acid:

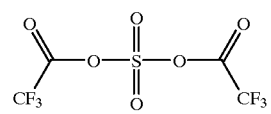

is produced in equilibria by contacting TFAA with sulfuric acid.

BRIEF SUMMARY OF THE INVENTION

We have developed a process for the preparation of alkanoate esters of hydroxybenzenesulfonic acids and salts thereof by a novel combination of esterification and sulfonation steps. The present invention provides a process for the preparation of an alkanoate esters of hydroxybenzenesulfonic acids and salts thereof (alkanoyloxybenzenesulfonic acid and salts thereof) by the steps comprising (1) contacting or reacting a phenol reactant with an alkanoic acid in the presence of trifluoroacetic acid (TFA) and trifluoroacetc anhydride (TFAA) to produce an aryl alkanoate ester and (2) contacting the reaction mixture of step (1) with a sulfonating agent to convert the aryl alkanoate ester to an alkanoate ester of hydroxybenzenesulfonic acid, i.e., alkanoyloxybenzenesulfonic acid. The alkanoyloxybenzenesulfonic acid may be treated with a basic compound such as an alkali metal or alkaline earth metal compound to convert the sulfonic acid to an alkali metal or alkaline earth metal salt. Alternatively, the step (2) sulfonation may be carried out in the presence of an alkali metal or alkaline earth metal sulfate to produce an alkali metal or alkaline earth metal sulfonate salt directly from step (2).

DETAILED DESCRIPTION

In the first step of the of the present invention a phenol reactant is contacted or reacted with an alkanoic acid in the presence of TFA and TFAA wherein the mole ratio of TFAA:phenol is about 3:1 to 0.1:1. The phenol reactant may be unsubstituted or substituted with one or more substituents such as unsubstituted or substituted hydrocarbyl, e.g., alkyl containing up to about 12 carbon atoms; hydroxy; alkoxy containing up to about 12 carbon atoms; alkoxycarbonyl containing 2 to about 12 carbon atoms; nitro; cyano; halogen; and the like. The phenol reactant preferably is unsubstituted phenol.

The alkanoic acid reactant may be an unsubstituted or substituted, saturated, aliphatic carboxylic acid containing a total of up to about 20 carbon atoms. The unsubstituted alkanoic acids typically contain 4 to 18, preferably about 6 to 16, carbon atoms. The alkanoic acid may be substituted with one or more, typically not more than one, substituent selected from alkoxy containing up to about 12 carbon atoms, halogen such as chloro and bromo, alkanoylamido containing up to about 12 carbon atoms, alkylsulfonamido containing up to about 12 carbon atoms. The alkanoic acid may be substituted with a second carboxyl group, e.g., adipic acid, azelaic acid and the like, which result in the formation of diphenyl dialkanoate esters. The alkanoic acid reactant preferably is an unsubstituted alkanoic acid containing about 6 to 16 carbon atoms or an alkanoic acid containing about 6 to 16 carbon atoms which is substituted with an alkanoylamido group containing up to about 12 carbon atoms. The preferred alkanoic acid reactant includes mixtures containing two or more alkanoic acids containing about 6 to 16 carbon atoms, e.g. a mixture containing approximately 4% hexanoic, 55% octanoic, 40% decanoic and 1% dodecanoic acids. The carboxylic acid and phenol may be used in carboxylic acid:phenol reactant mole ratios in the range of about 2:1 to 0.5:1, preferably about 1.2:1 to 0.8:1.

TFAA is employed in the first step in an amount which gives a TFAA:phenol reactant ratio of about 3:1 to 0.1:1, preferably about 1.5:1 to 0.75:1. The amount of TFA solvent present initially and during the operation of the first step of the process of the present invention typically gives a TFA:phenol mole ratio of at least 0.1:1 and preferably a TFA:phenol mole ratio in the range of about 0.5:1 to 20:1. Such mole ratios typically provide preferred amounts of TFA greater than 15 weight percent based on the weight of the phenol, carboxylic acid and TFAA present. The amount of TFA present preferably is in the range of about 25 to 75 weight percent based on the weight of the phenol, carboxylic acid and TFAA present. Other inert solvents may be used in conjunction with TFA. Examples of such solvents include halogenated hydrocarbons such as dichloromethane and dichlorobenzene, etherial solvents such as dioxane and polar aprotic solvents such as dimethylformamide. Benefits of such co-solvents may be obtained in step (2) of the process of the present invention in which such additives may function as "complexing agents" to modify the selectivity of the sulfonating agent. The benefits of such complexing agents are noted in U.S. Pat. No. 4,695,412 and incorporated herein by reference.

Step (1) of the process may be carried out over a broad range of temperatures, e.g., temperatures of about −30 to 250° C. although the use of lower temperatures, e.g., temperatures in the range of about −10 to 80° C., are preferred to attain high product quality due to the avoidance or minimization of the formation of color bodies. Pressure is not an important aspect of step (1) and, thus, the step (1) may be carried out at pressures moderately above or below ambient pressure.

Step (2) of the present process comprises contacting the reaction mixture of step (1) with a sulfonating agent, i.e. a source of sulfur trioxide, to convert the aryl alkanoate ester to an alkanoate ester of hydroxybenzene-sulfonic acid. The product of the sulfonation reaction consists of, or primarily of, the 4-isomer, e.g., 4-(alkanoyloxy)benzenesulfonic acid. Step (2) of the process preferably comprises contacting the reaction mixture of step (1) with either (i) sulfur trioxide or (ii) fuming sulfuric acid, e.g., a 10 to 70 weight percent solution of sulfur trioxide in sulfuric acid. In the first, and most preferred, embodiment the sulfonating agent is sulfur trioxide. In this embodiment the amount of sulfur trioxide employed gives a mole ratio of $SO_3$:phenol reactant of about 1.2:1 to 0.8:1 but it is preferred to minimize the excess of sulfur trioxide. A ratio of $SO_3$:phenol reactant in the range of 1.05:1 to 0.95:1 is thus preferred. In a second preferred embodiment of step (2) fuming sulfuric acid is employed as the sulfonating agent. In this embodiment, TFAA is further added to the fuming sulfuric acid in an amount to produce a 1:1 mole ratio of TFAA:sulfuric acid. TFAA is thus combined with fuming sulfuric acid to give a TFAA:fuming sulfuric acid weight ratio of about 3:1 to about 0.5:1, depending, for example, on the concentration of sulfur trioxide in the sulfuric acid. The amount of fuming sulfuric acid used usually will be any amount which provides one mole of sulfur trioxide per mole of phenol reactant used in the first step.

The sulfonation of step (2) may be carried out at a temperature of about −20 to 100° C., preferably about 0 to 80° C. At the conclusion of the step (2) reaction, the alkanoyloxybenzenesulfonic acid product may be recovered by vaporizing and removing the volatile material present. Reduced pressure may be used to facilitate the removal of the volatile materials or other methods such as spray-drying or fluidized-bed drying. The alkanoyloxybenzenesulfonic acid product resulting from the first two embodiments of step (2) may be neutralized with an alkali metal or alkaline earth metal base such as a hydroxide, carbonate or bicarbonate to convert the sulfonic acid to an alkali metal or alkaline earth metal sulfonate salt wherein the neutralization is carried out from 10 to 40° C. The potassium and sodium salts are preferred. Alternatively, the step (2) product may be obtained directly as an alkali metal or alkaline earth metal sulfonate salt by performing the step (2) sulfonation in the presence of an alkali metal or alkaline earth metal sulfate or bisulfate or any combination of an alkali metal or alkaline earth salt and sulfur trioxide, oleum and/or sulfuric acid. The amount of alkali metal or alkaline earth salt employed normally will be at least one equivalent of alkali metal or alkaline earth cation per mole of desired sulfonic acid product. This alternative approach produces the alkanoyloxybenzenesulfonate salt without further treatment and may be preferred in certain cases.

An advantage of the process is its applicability to mixtures of carboxylic acids. Because fatty acids (especially from natural sources) are often obtained as mixtures of carboxylic acids, the ability to convert such a mixture to its corresponding mixture of benzenesulfonate esters offers a great advantage to a manufacturer that wishes to utilize such low cost feedstocks. For example, a mixture of alkanoic carboxylic acids known as C-810 is available from Procter & Gamble Chemicals. This mixture contains about 4% hexanoic, 55% octanoic, 40% decanoic and 1% dodecanoic acids. As described above, TFA is readily removed by evaporation under mild conditions so purification of the products to high purity white powders is vastly simplified in contrast to processes described in the art which rely on crystallization and filtration to purify benzenesulfonate esters. Such methods, when applied to a mixture of benzenesulfonate esters, are complicated by variable rates of crystallization that exist for different benzenesulfonate ester products. The embodiment of the present invention is readily applied to the manufacture of products containing a mixture of benzenesulfonate esters.

A further advantage of the present invention is the efficiency with which it converts primary raw materials to benzenesulfonate esters. Alkanoic acids rather than anhydrides or acid halides are preferred, although it is recognized that such materials might be substituted for alkanoic acids in less desirable variations of the present invention. Likewise, by carrying out the sulfonation of an aryl ester, rather than sulfonating phenol, the separate manufacture of SPS is avoided. The net process of converting carboxylic acids to their respective hydroxy-benzenesulfonate esters is thus economically simplified.

EXAMPLES

The process provided by the present invention is further illustrated by the following examples. $^1$H NMR spectra were obtained on a Varian Gemini 300 NMR spectrometer with samples dissolved in $d_6$-DMSO and chemical shifts referenced to the pentet centered at δ2.50 ppm vs TMS due to residual protons in $d_6$-DMSO.

EXAMPLE 1

Step (1)—Esterification

Octanoic acid (24.58 g, 0.170 moles) and phenol (15.79 g, 0.167 moles) were placed in a dry 300-ml, three-neck flask fitted with a Friederich condenser and rubber septa under an argon atmosphere. TFA (100 ml) was added and the solution was cooled with an ice-bath. TFAA (moles) was added by syringe and the solution was allowed to stir for thirty minutes at a temperature of about 0 to 5° C. A 10 ml sample was withdrawn and the volatiles were stripped on a rotary evaporator to yield 2.50 g of crude product residue. Analysis by $^1$H NMR of this residue revealed nearly complete conversion of the phenol to phenyl octanoate (a slight amount, e.g., ≈10%, of unreacted phenol remained). An additional aliquot (3.7 g) of TFAA was added to the solution and allowed to stir an additional thirty minutes at 0–5° C.

Step (2)—Sulfonation

Oleum (0.5 ml of 18–24%, ≈10.0 millimoles—mmol) and TFAA (3.0 ml, 21 mmol) were combined in a 100 ml two-neck flask cooled by an ice-bath under an argon atmosphere. After ten minutes a 10 ml aliquot of phenyl octanoate/TFA solution from Step (1) (11.0 mmol) was added by syringe to this solution and the mixture was stirred for fifteen minutes at a temperature of about 0–5° C.. The volatiles were stripped on a rotary evaporator leaving 3.51 g. of a light orange oil. Analysis by $^1$H NMR showed conversion of phenyl octanoate to its benzenesulfonate ester, recognized by the characteristic doublets at δ7.61 and 7.05 ppm in the aromatic region of its NMR spectrum. $^1$H NMR: δ7.61, d (8.8, 2H); 7.05, d (8.7, 2H); 2.57, t (7.1, 2H); 1.64, m (2H); 1.37 (8H) and 0.87, t (3H).

The oil from step (2) was treated with $K_2CO_3$ (0.835 g, 6.0 mmol) dissolved in 10 ml of water. A small sample was dried yielding a white powder which was shown by $^1$H NMR analysis to be essentially identical to the material described above.

EXAMPLE 2

Oleum (0.25 ml of 18–24%, ≈5 mmol), $K_2SO_4$ (0.30 g, 5 mmol) and TFAA (3.0 ml, 21 mol) were combined in a 100 ml two-neck flask cooled by an ice-bath under an argon atmosphere. After fifteen minutes a 10 ml aliquot of phenyl octanoate/TFA solution from step (1) of Example 1 (11 mmoles) was added by syringe to this solution and the mixture was stirred for one hour. Volatile materials were stripped on a rotary evaporator leaving a light brown residue. $^1$H NMR of this material indicated conversion of phenyl octanoate to potassium 4-(octanoyloxy) benzenesulfonate. Treatment of the residue with 30 ml of acetone produced a white solid which was dried on a Buchner funnel yielding 1.27 g of product (34% yield).

EXAMPLE 3

Oleum (1.77 g of 18–24%, ≈17.6 mmol) TFAA (3.0 ml, 21 mmol) and 5 ml. of TFA were combined in a 100 ml two-neck flask cooled by an ice-bath under an argon atmosphere. After ten minutes phenyl acetate (3.5 g, 25.7 mmol) dissolved in 5 ml. of TFA was added by syringe and the mixture was stirred for fifteen minutes. Sodium trifluoroacetate (3.6 g, 26 mmol) was added under an argon flow and the volatiles were stripped on a rotary evaporator. Analysis by $^1$H NMR showed conversion of phenyl acetate to sodium 4-(acetoxy)benzenesulfonate, recognized by the characteristic doublets at δ7.61 and 7.05 ppm in the aromatic region of its NMR spectrum.

The invention has been described in detail with particular reference to preferred embodiments thereof, but it will be understood that variations and modifications can be effected within the spirit and scope of the invention.

We claim:

1. A process for the preparation of an alkanoate ester of a hydroxy-benzenesulfonic acid and salts thereof by the steps comprising (1) contacting a phenol reactant with an alkanoic acid in the presence of trifluoroacetic acid (TFA) and trifluoroacetic anhydride (TFAA) to produce a aryl alkanoate ester and (2) contacting the reaction mixture of step (1) with a sulfonating agent to convert the aryl alkanoate ester to an alkanoyloxy-benzenesulfonic acid or salt thereof.

2. A process according to claim 1 wherein step (1) is carried out at a temperature of about −10 to 80° C.; step (2) is carried out at a temperature of about 0 to 70° C.; and the alkanoic acid is an unsubstituted or substituted carboxylic acid containing a total of up to about 20 carbon atoms.

3. A process according to claim 2 wherein the amount of TFA present in step (1) gives a mole ratio of TFA:phenol reactant of about 0.5:1 to 20:1 and the amount of TFAA present in step (1) gives a mole ratio of TFAA:phenol of about 1.5:1 to 0.75:1.

4. A process according to claim 3 wherein the sulfonating agent in step (2) is selected from (i) sulfur trioxide in a mole ratio of $SO_3$:phenol reactant of about 1.2:1 to 0.8:1 or (ii) a combination of fuming sulfuric acid and TFAA in which the amount of TFAA gives a 1:1 mole ratio of TFAA:$H_2SO_4$ and the amount of fuming sulfuric acid provides one mole of sulfur trioxide per mole of phenol reactant.

5. A process according to claim 4 wherein the alkanoic acid is an unsubstituted alkanoic acid containing about 6 to 16 carbon atoms; the amounts of fuming sulfuric acid and TFAA employed in step (2) give a TFAA:fuming sulfuric acid weight ratio of about 3:1 to about 0.5:1; and the product comprises an alkanoate ester of 4-hydroxybenzenesulfonic acid.

6. A process according to claim 4 wherein the alkanoic acid is an alkanoic acid containing about 6 to 16 carbon atoms which is substituted with an alkanoylamido group containing up to about 12 carbon atoms; the amounts of fuming sulfuric acid and TFAA employed in step (2) give a TFAA:fuming sulfuric acid weight ratio of about 3:1 to about 0.5:1; and the product comprises an alkanoate ester of 4-hydroxybenzenesulfonic acid.

7. A process according to claim 4 wherein the alkanoic acid comprises a mixture of unsubstituted alkanoic acids containing about 6 to 16 carbon atoms; the amounts of fuming sulfuric acid and TFAA employed in step (2) give a TFAA:fuming sulfuric acid weight ratio of about 3:1 to about 0.5:1; and the product comprises alkanoate esters of 4-hydroxybenzenesulfonic acids.

8. A process according to claim 4 wherein the alkanoic acid comprises a mixture of alkanoic acids containing about 6 to 16 carbon atoms substituted with alkanoylamido groups containing up to about 12 carbon atoms; the amounts of fuming sulfuric acid and TFAA employed in step (2) give a TFAA:fuming sulfuric acid weight ratio of about 3:1 to about 0.5:1; and the product comprises alkanoate esters of 4-hydroxybenzenesulfonic acids.

9. A process according to claim 4 wherein the alkanoic acid is an unsubstituted alkanoic acid containing about 6 to 16 carbon atoms; the amounts of fuming sulfuric acid and TFAA employed in step (2) give a TFAA:fuming sulfuric acid weight ratio of about 3:1 to about 0.5:1; step (2) is carried out in the presence of an alkali metal or alkaline earth metal sulfate to produce an alkali metal or alkaline earth metal salt comprising an alkanoate ester of 4-hydroxybenzenesulfonic acid salt.

10. A process according to claim 4 wherein the alkanoic acid is an alkanoic acid containing about 6 to 16 carbon atoms which is substituted with an alkanoylamido group containing up to about 12 carbon atoms; the amounts of fuming sulfuric acid and TFAA employed in step (2) give a TFAA:fuming sulfuric acid weight ratio of about 3:1 to about 0.5:1; step (2) is carried out in the presence of an alkali metal or alkaline earth metal sulfate to produce an alkali metal or alkaline earth metal salt comprising an alkanoate ester of 4-hydroxybenzenesulfonic acid salt.

11. A process according to claim 4 wherein the alkanoic acid comprises a mixture of unsubstituted alkanoic acids containing about 6 to 16 carbon atoms; the amounts of fuming sulfuric acid and TFAA employed in step (2) give a TFAA:fuming sulfuric acid weight ratio of about 3:1 to about 0.5:1; step (2) is carried out in the presence of alkali metal or alkaline earth metal sulfates to produce alkali metal or alkaline earth metal salts comprising alkanoate esters of 4-hydroxybenzenesulfonic acid salts.

12. A process according to claim 4 wherein the alkanoic acid comprises a mixture of alkanoic acids containing about 6 to 16 carbon atoms which are substituted with alkanoylamido groups containing up to about 12 carbon atoms; the amounts of fuming sulfuric acid and TFAA employed in step (2) give a TFAA:fuming sulfuric acid weight ratio of about 3:1 to about 0.5:1; step (2) is carried out in the presence of alkali metal or alkaline earth metal sulfates to produce alkali metal or alkaline earth metal salts comprising alkanoate esters of 4-hydroxybenzenesulfonic acid salts.

* * * * *